United States Patent [19]

Schaeffer et al.

[11] Patent Number: 5,604,096

[45] Date of Patent: Feb. 18, 1997

[54] FLUOROMETRIC QUANTITATION OF MYCOPLASMAS

[76] Inventors: Warren I. Schaeffer, 24 Southwind Dr.; Robert Melamede, 49 Peru St., both of Burlington, Vt. 05401

[21] Appl. No.: 302,250

[22] Filed: Sep. 8, 1994

Related U.S. Application Data

[63] Continuation of Ser. No. 26,565, Mar. 4, 1993, abandoned.

[51] Int. Cl.$^6$ .............................. C12Q 1/68; C12Q 1/18
[52] U.S. Cl. .................................. 435/6; 435/32
[58] Field of Search ............................ 435/6, 32

[56] References Cited

U.S. PATENT DOCUMENTS 2,662,082  12/1953  Short et al. ........................... 546/108

FOREIGN PATENT DOCUMENTS

WO92/03157  3/1992  WIPO .

OTHER PUBLICATIONS

Valle et al. (1981) "Fluorometric Determination of DNA & RNA in Chlamydamonas using Ethidium Bromide" J Biochem Biophys Meth. 4:271–277.

Le Pecq et al. (1966) "A New Fluorometric Method for RNA & DNA Determination" Anal. Biochem. 17: 100–107.

Halprin et al. (1979) A combined Alkali extraction–Ethidium Bromide Technique for the Measurement of DNA in Small Pieces & Tissue. J. Invest. Dermat. 73:359–363.

LePecq et al. (1967) "A Fluorescent Complex between Ethidium Bromide and Nucleic Acids" J. Mol. Biol 27:87–106.

Sambrook et al. (1989) Molecular Cloning: A Laboratory Manual, Cold Spring Harbor, NY: Cold Spring Harbor Laboratory Press. Appendix E5.

Latt et al., "Fluorescent Probes of DNA Microstructure and DNA Synthesis" *Flow Cytometry and Sorting*, Second Edition pp. 249–290 (1990).

Kowalski "A Procedure for the Quantitation of Relaxed Closed Circular DNA in the Presence of Superhelical DNA: An Improved Fluorometric Assay for Nicking–Closing Enzyme" Analytical Biochemistry 1979, vol. 93, pp. 346–354.

*Primary Examiner*—Jasemine C. Chambers
*Assistant Examiner*—Scott D. Priebe
*Attorney, Agent, or Firm*—Lahive & Cockfield; Jane E. Remillard

[57] ABSTRACT

The present invention pertains to methods of monitoring mycoplasmal growth whereby a culture of mycoplasmal cells is contacted with a fluorescent nucleic acid-binding agent under conditions which allow the agent to selectively bind to mycoplasmal nucleic acid. The amount of fluorescence associated with the mycoplasmal nucleic acid indicates the number of mycoplasmal cells in the culture. The fluorescence of the culture is typically read using a fluorometer which correlates with colonial growth on agar. A particularly preferred fluorescent nucleic acid-binding agent is ethidium bromide. The present invention further pertains to methods of determining the effectiveness of an antimycoplasmal antibiotic.

13 Claims, 5 Drawing Sheets

FLUOROMETRIC QUANTITATION OF MYCOPLASMAS

This application is a continuation of application Ser. No. 08/026,565 filed on Mar. 4, 1993, now abandoned, the contents of which is expressly incorporated by reference.

BACKGROUND OF THE INVENTION

Members of the genera Mycoplasma (a genus requiring sterols) and Acholeplasma (a genus capable of growth without sterols), hereinafter referred to as mycoplasma, are the smallest (0.2 to 2 μm in diameter (Hay, R. J. et al., (1989) *Nature* 339:4)), and the simplest free-living parasitic organisms known. Mycoplasmas differ from bacteria in lacking cell walls and possess the smallest recorded genome in living cells, from $0.5 \times 10^9$ to $1.0 \times 10^9$ Da (Lo, S.-C et al., (1991) *Science* 251:1074–1076; and Razin, S., (1985) *Microbiol. Revs.* 49:419–455). Mycoplasma are known to infect both animals and plants causing, or being implicated in the cause of, a variety of diseases (Brown, T. et al., (1970) *Trans. Amer. Clin. and Climatol. Assn.* 82:227–247; Brown, T. et al., (1973) Internal Congress On Rheumstology, Vol. XIII, Amsterdam: Elsevier/Excerpta Medica, p. 172 (International congress series No. 299); Chowdhury, M. I. H. et al., (1990) *Biochem. Biophys. Res. Comm.* 170:1385–1370; Clark, H. W., (1991) *Amer. J. Primatol.* 24:235–243; Kundsin, R. B. et al., (1981) *Science* 213:474–478; Lemsitre, M. et al. (199) *Res. Virol.* 141:5–16; LeMaitre, M. et al., (1992) *Inf. and Immun.* 600:742–748; Lo, S-C. et al., (1989) *Am. J. Trop. Med. Hyg.* 41:586–600; Lo, S.-C. et al., (1991) *Science* 251:1074–1076; Saillard, C. et al., (1990)*Res. Virol.* 141:385–395; and Wright, K., (1990) *Science (Research News)* 248:682–683). Therefore, the of the mechanism of the activity of mycoplasma is important.

Many species of mycoplasmas can be grown axenically in broth media containing undefined, exotic additives. However, the quantitation of broth-grown mycoplasmas has been a problem. Unlike broth cultures of larger bacteria, in which turbidity parallels growth and which, therefore, can be quantified turbidimetrically, cultures of many mycoplasmas have reached peak growth before turbidity is apparent. Where pH changes occur in mycoplasmal cultures, a color change in the media is often used to indicate peak growth. However, not all mycoplasmas cause a medium color change and if so, such a change may not coincide with peak growth. Colonial growth on agar is one method of quantitation which has the drawback that the data is always obtained retrospectively, as the original culture is gone by the time colonies are of a size sufficient for quantitation. These difficulties have hampered the standardization of cultures within and between laboratories and the development of new and defined media for cultivation. Moreover, the evaluation of antimycoplasmal agents and the general understanding of mycoplasmal growth characteristics has been hindered due to a lack of an accurate real time quantitative assay. The necessity of using complex and undefined media to grow mycoplasmas precludes any rapid development of mutants important in analysis of mycoplasmal pathogenesis. An assay for the quantitation of mycoplasmal growth and the study of antimycoplasmal agents would be beneficial.

SUMMARY OF THE INVENTION

The present invention pertains to methods of monitoring mycoplasmal growth whereby a culture of mycoplasmal cells is contacted with a fluorescent nucleic acid-binding agent under conditions which allow the agent to selectively bind to mycoplasmal nucleic acid. The amount of fluorescence associated with the mycoplasmal nucleic acid indicates the number of mycoplasmal cells in the culture. The fluorescence of the culture is typically read using a fluorometer which correlates with colonial growth on agar. Thus, the fluorometric readings allow an estimation of the colony-forming-units present in the culture at any time. Although there are a wide variety of fluorescent nucleic acid-binding agents useful in methods of the invention, a DNA intercalating agent such as a phenanthridinium dye is preferred. The term "intercalation" is used to describe the insertion of planar aromatic (or heteroaromatic) compounds between adjacent base pairs of double stranded DNA. A particularly preferred phenanthridinium dye is ethidium bromide.

The present invention further pertains to methods of determining the effectiveness of an antimycoplasmal antibiotic whereby a culture of mycoplasmal cells containing the antibiotic is contacted with a fluorescent nucleic acid-binding agent under conditions which allow the agent to selectively bind to mycoplasmal nucleic acid. The amount of fluorescence associated with the mycoplasmal DNA indicates the number of mycoplasmal cells in the culture and permits an assessment of the effectiveness of the mycoplasmal antibiotic.

Use of the methodology of the present invention will permit investigators to ascertain the phase of the growth cycle of a mycoplasmal culture concomitant with the growth of the culture. Moreover, since fluorometer readings of culture aliquots can be converted to DNA equivalents, the standardization of mycoplasmal cultures within and between laboratories is possible.

DETAILED DESCRIPTION

Figure 1:
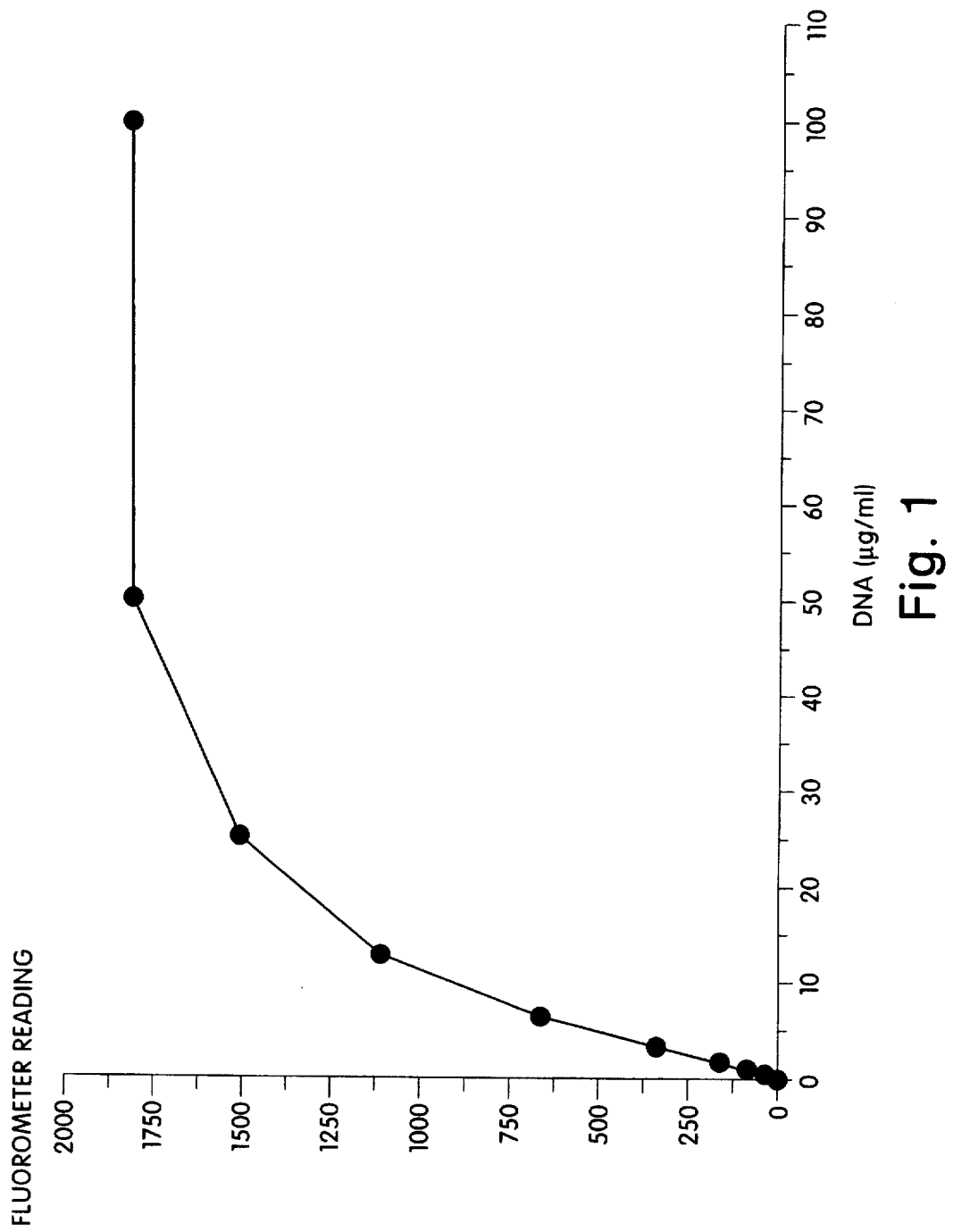
FIG. 1 is a DNA standard curve prepared using purified salmon testes DNA in concentrations ranging from 0 to 100 μg/ml in an alkaline ethidium bromide solution in which the fluorescence of the resulting solution was determined.

The present invention pertains to methods of monitoring mycoplasmal growth whereby a culture of mycoplasma is contacted with an amount of a fluorescent nucleic acid-binding agent under conditions which allow the agent to selectively bind to mycoplasmal nucleic acid. The amount of fluorescence associated with the mycoplasmal nucleic acid indicates the number of mycoplasma cells in the culture at any given time.

The term "fluorescent nucleic acid-binding agent" is intended to include agents which selectively bind DNA or RNA with a resulting fluorescence that is detectable. Such fluorescent nucleic acid-binding agents include intercalating and non-intercalating agents (e.g., A-T base-specific agents). Particularly preferred fluorescent nucleic acid-binding agents are DNA intercalating agents whose primary binding depends on the double-helical polynucleotide structure. Such agents can be mono- or polyintercalators which insert between adjacent base pairs of double-stranded DNA. A preferred group of DNA intercalating agents is phenanthridinium dyes such as ethidium, ethidium bromide, propidium and the ethidium homodimer (a polyintercalator; see *Nature* (1992) 359:859–860). Other fluorescent nucleic acid-binding agents within the scope of the invention include acridine dyes (e.g., acridine orange, proflavine, acriflavine, quinacrine, and 2,7-di-t-butylproflavine), bisbenzimidazole dyes (e.g., 33258 Hoechst) and other related A-T base-specific dyes such as DAPI (4',6-diamidino-2-phenylindole). Additional bisbenzimidazole dyes and other A-T base-specific dyes are described in *Flow Cytometry and Sorting*, 2nd Edition, pp. 249–290, 1990, Wiley-Liss, Inc.

As a preferred group of fluorescent DNA intercalating agents, the family of phenanthridinium dyes (described in U.S. Pat. No. 2,662,082, incorporated herein by reference) can be represented by the formula:

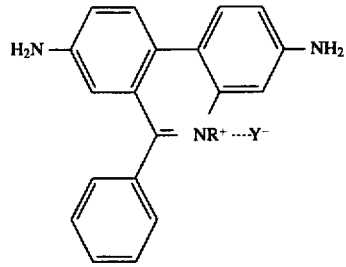

wherein R is selected from the group consisting of hydrogen, alkyl, alkenyl, alkynyl, alkoxy and haloalkyl and Y represents an anion. The alkylene, alkenylene, alkynylene, alkyl, alkenyl and alkynyl groups (hereinafter hydrocarbon groups) may have straight or branched chains. The unsaturated groups may have a single site of unsaturation or a plurality of sites of unsaturation. The hydrocarbon groups preferably have up to about ten carbons, more preferably up to about six carbons, and most preferably up to about three carbons. A hydrocarbon group having three carbon atoms or less is considered to be a lower hydrocarbon group. For example, an alkyl group having three carbon atoms or less is a lower alkyl. Examples of lower hydrocarbon groups which may be used in the present invention include methyl, methylene, ethyl, ethylene, ethenyl, ethenylene, ethynl, ethynlene, propyl, propylene, propenyl, propenylene, propynyl, and propynylene. Examples of higher hydrocarbon groups from (four to about ten carbons) include butyl, t-butyl, butylene, butenyl, butenylene, and butynyl, butynylene, nonyl, nonylene, nonenyl, nonenylene, nonynyl, and nonynylene.

The alkoxy, haloalkyl, alkoxyene, and haloalkylene groups (hereinafter substituted hydrocarbon groups) are alkyl or alkylene groups substituted with one or more oxygen or halogen atoms. The alkoxy and haloalkyl groups also may be straight or branched chain and preferably are made up of up to about ten atoms (including carbon, oxygen or halogen), preferably up to about six atoms, and most preferably up to about three atoms. The term halogen is art-recognized and includes chlorine, fluorine, bromine, and iodide. Examples of substituted hydrocarbon groups which are useful within this invention are similar to the examples of the hydrocarbon groups set forth above except for the incorporation of oxygen(s) or halogen(s) into the groups.

Preferred members of the phenanthridinium dye family include a well-known substance ethidium (also known as: 3,8-diamino-5-ethyl-6-phenylphenanthridinium; 2,7-diamino-9-phenyl-10-ethylphenanthridinium; 2,7-diamino-10-ethyl-9-phenylphenanthridinium; and homidium) (see *The Merck Index* 10th edition, No. 4625 (1983)) whose formula is as follows:

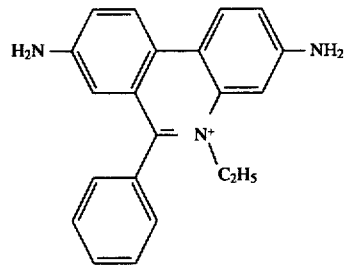

A particularly preferred member of the anthridinium dye family for use in methods of the present invention is ethidium bromide (also known as 2,7-diamino-9-phenyl-10-ethylphenanthridinium bromide) which has the following formula:

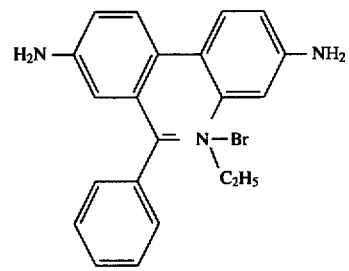

Phenanthridinium dyes such as ethidium, ethidium bromide and propidium are commercially available and further may be chemically synthesized using conventional techniques such as those described in U.S. Pat. No. 2,662,082. The family of phenanthridium dyes is intended to include compounds which are structurally similar, compounds which are art-recognized as being analogs, and/or compounds which share the same or similar function.

Ethidium bromide is a particularly preferred fluorescent DNA intercalating agent for use in the subject invention. The binding of ethidium bromide to DNA is associated with a shift in dye absorption from 480 nm to 520 nm and a marked increase in fluorescence efficiency. Unlike the bisbenzimidazole dye 33258 Hoechst which is one of several A-T, specific molecules that bind tightly to DNA without intercalation, ethidium bromide binding to nucleic acid depends little on the acid base composition. The 33258 Hoechst dye possesses a long wavelength absorption maximum near 340 nm at pH7, with flourescence emission peaking slightly above 500 nm. Flourescence of this dye when complexed with DNA varies with the DNA A-T content. The 33258

Hoechst compound and other related A-T base-specific dyes such as DAPI (4',6-di-amidino-2-phenylindole) can be used in methods of the invention but are not preferred due to their A-T specificity. In addition, the 33258 Hoechst compound binds weakly to RNA and exhibits less flourescence than when bound to DNA.

Ethidium bromide is also preferred for use in methods of the invention due to its greater stability and ease of use when compared to the 33258 Hoechst compound. For example, the 33258 Hoechst dye was found to require fixation or cell damage in order to achieve fluorescent staining of DNA due to its inability to penetrate living cells. Additionally, studies comparing the efficacy of ethidium bromide and the 33258 Hoechst in methods of the invention demonstrated that the Hoechst compound dye failed to produce consistent results.

Thus, according to one aspect of the invention, the growth of mycoplasma in a culture is monitored by contacting the culture with an amount of a fluorescent nucleic acid-binding agent. For example, a sample from a mycoplasmal culture can be removed and concentrated, such as by centrifugation and the supernatant removed. The concentrated sample can be resuspended and a solution containing an amount of a fluorescent nucleic acid-binding agent can be added under conditions appropriate for binding of the agent to mycoplasmal nucleic acid. When ethidium bromide is used as the fluorescent nucleic acid-binding agent, both DNA and RNA can be selectively targeted and the resulting fluorescence quantitated using standard techniques. Excitation sources, such as the Filter Fluorometer manufactured by Optical Technology Devices, Inc. are well known in the art and can be selected based on the instrumental capabilities desired. The culture conditions are selected to permit the fluorescent nucleic acid-binding agent to bind mycoplasmal nucleic acid selectively such that an accurate measurement of cell population can be made. To selectively target mycoplasmal DNA, an amount of an ethidium bromide is added to a culture under alkaline conditions sufficient to degrade RNA. To prevent contribution of RNA to ethidium bromide binding, the culture can be maintained at a pH of about 10 to about 13 and preferably at a pH of about 11 to about 12 to degrade RNA.

Other binding agents, such as the 33258 Hoechst compound may require treatment of the cells in order to achieve binding of the dye to mycoplasmal nucleic acid. As previously stated, the mycoplasmal cells may need to be fixed or in some way damaged (e.g., with alcohol treatment) in order to allow 33258 Hoechst binding to mycoplasmal DNA.

Culture conditions for maintaining viable mycoplasmal cells are well known in the art and depend in part on the species of mycoplasma selected. For example, most species of mycoplasma are broth-grown and require a sterol and serum protein for growth. Other additives to broth such as nucleic acid precursors, vitamins, starch and mucin may be necessary. For solid medium, 1% agar is typically used. Most species of mycoplasma can be cultivated areobically, but some may require nitrogen with 5–10% $CO_2$.

The present invention also pertains to methods of determining the effectiveness of an antimycoplasmal antibiotic. For example, mycoplasmal cells cultured with an antimycoplasmal antibiotic to be tested are contacted with a fluorescent nucleic acid-binding agent (such as the DNA intercalating agent ethidium bromide) under conditions which allow the agent to selectively bind mycoplasmal nucleic acid. The amount of fluorescence associated with the mycoplasmal nucleic acid indicates the number of mycoplasmal cells in the culture and, thus, the relative effectiveness of the antibiotic. A known antibiotic, such as chloramphenicol succinate, can be tested to determine sensitivity of a particular mycoplasmal strain to the antibiotic. The method of the invention can also be used to optimize medium components to develop more defined media or novel media compositions than those currently available for mycoplasmal growth.

The present invention is further illustrated by the following examples which should not be construed as further limiting. The contents of all references, published patent applications and patents cited throughout this application are hereby incorporated by reference.

EXAMPLE 1

Development of a Fluorometric System and Standard DNA Curve

A fluorometric system for broth-grown mycoplasma was developed as a modification of the system of Kowalski ((1979) Anal. Biochem, 93:346–354) originally devised as a differential fluorescence system for detecting nicked vs. intact circular DNA. The relationship of DNA concentration to fluorometer reading for a purified DNA sample (via a standard curve) and for various mycoplasmal culture samples was determined. The method is based upon the ability of ethidium bromide to bind to DNA in an alkaline solution where the pH is sufficient to degrade RNA and to thereby exclude any contribution due to RNA.

*Mycoplasma fermentans* (PG-18) or *Mycoplasma hyorhinis* (isolated from an infected cell culture) was grown in a modification of SP-4 Medium originally described by Tully, et al. (1977, Science 195:892–894) at 37° C. and 5% $CO_2$. The yeast extract used was freshly prepared according to the methodology of Kotani, et al. ((1990) In *Vitro Cell. Devl. Biol.* 26:91–96). The medium was assembled by mixing the freshly prepared basal portion together with all of the additives and the complete medium was then filter-sterilized through a 0.22 μM filter. No part of the medium was autoclaved. Glucose, especially, was always filter-sterilized because of the potential for generation of toxic products when glucose is autoclaved (Stanier, R. Y., (1942) *Soil Sci.* 53:479) in the presence of phosphates. Because fluorometric analysis is being used, no additional phenol red was added to the medium beyond that which is present due to the CMRL 1066 medium additive called for in the SP-4 recipe. For agar growth, a 10% noble agar solution was prepared in distilled water, autoclaved and dispensed into suitable aliquots so that when remelted it could be added to sufficient complete medium to yield 1% agar. 60 mm petri plates were then poured with 5 ml of the agar/medium mixture. 0.1 ml of culture dilutions were spread over the surface of the agar before incubation at 37° C. and 5% $CO_2$.

To monitor the growth of mycoplasma, a 0.5 ml sample was removed from a broth culture and placed into a microcentrifuge tube along with 0.5 ml of Dulbecco's Phosphate-Buffered Saline (PBS) (GIBCO, Grand Island, N.Y.), which can, if desired, contain EDTA. The sample was centrifuged at 15,000 rpm for 10 minutes at 4° C. The supernate was removed, the pellet resuspended in 0.5 ml of PBS and transferred to a small test tube. The microcentrifuge tube was then washed with another 0.5 ml of PBS which was added to the resuspended pellet. 2.0 ml of an ethidium bromide (EtBr) solution [1.0 μg/ml EtBr; 0.5 Mm EDTA; 20 Mm $KH_2PO_4$; final pH of 11.8–12.0 adjusted with 5M KOH] was then added to the test tube. The fluorescence of the resulting solution was read in an Optical Technology Devices, Inc. Model Ratio-2 System Filter Fluorometer (No.

154910) against a medium blank which was processed as though it were inoculated. A 500 ng sample of DNA (which reads in the linear portion of a DNA standard curve) was used as an internal standard for the fluorometer. This permits conversion of fluorometer readings to DNA equivalents. It should be noted that once the alkaline EtBr solution is added to the cultural aliquot, the sample can be stored at 4° C., should this be required, provided it is protected from light.

A standard curve of DNA was prepared using purified salmon testes DNA (Sigma Chemical Corp.) in concentrations ranging from 0 to 100μg/ml. FIG. 1 illustrates the data received from one of several standard curves and indicates that there is linearity within the range of 0–20 μg/ml. There is a change in slope between 20 and 50 μg/ml after which the curve becomes saturated. Based upon the standard curve, a 500 ng/ml sample of DNA is always used during assays to standardize the fluorometer. Such a sample normally reads between 20 and 30 fluorometer units which is consistent with the standard curve.

To determine whether a given fluorometer reading from a cultural sample is due primarily to DNA present in the cells a sample from a mycoplasmal culture was obtained during the early portion of the growth curve prior to a significant pH change or medium precipitation. The genome size of $M.$ $fermentans$ is reported to be $4.8 \times 10^8$ da (Razin, S. et al., (1983) Yale J. Biol. and Med. 56:357–366), and since 1 da is equivalent of $1.67 \times 10^{-24}$ g, the genome of a single $M.$ $fermentans$ is $8.016 \times 10^{-10}$ μg. A 24 hr culture was sampled and assayed in the fluorometric system as described above. A reading of 533±55 was obtained. The number of colony-forming-units (cfu) present in this sample was $9.6 \times 10^9$ cfu/ml. Since one cell contains $8.016 \times 10^{-10}$ μg, $9.6 \times 10^9$ cfu would contain 7.8 μg DNA. From the standard curve, 7.8 μg of DNA should yield a fluorometer reading of 598 and, as noted above, a reading of 533±55 was obtained which is within experimental error. A similar correlation existed for $M.$ $hyorhinis$ when it was examined.

Figure 2:
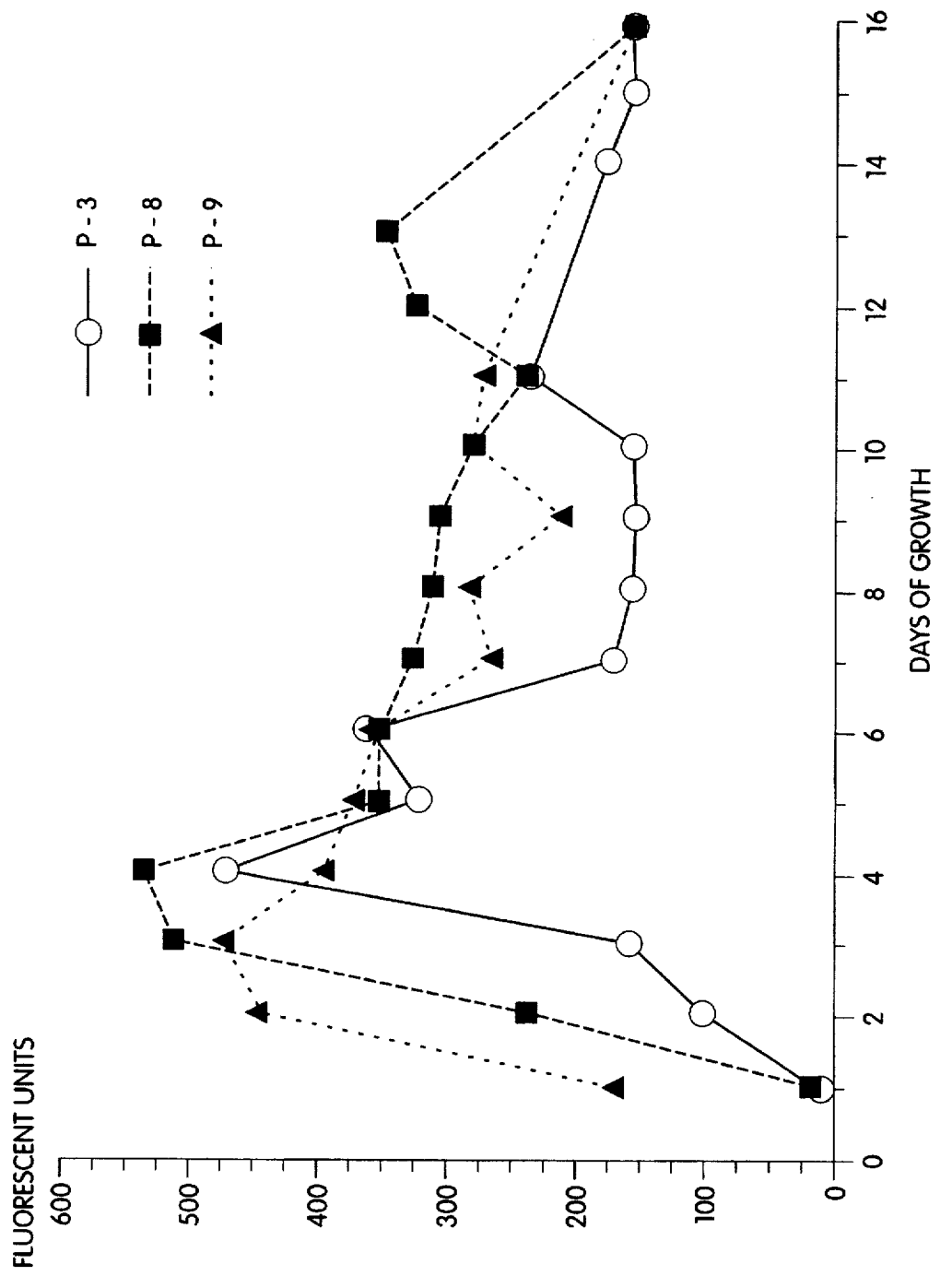
FIG. 2 depicts fluorometric monitoring of the three successive passages of *M. hyorhinis* over various days of growth. The fluorometric readings correlate with colonial growth on agar. The symbols depict three separate cultures.

FIG. 2 demonstrates the consistency and reproducibility of the fluorometric system in determining growth kinetics. Three separate cultures of $M.$ $hyorhinis$ grown over a period of 16 days as described above, demonstrated essentially the same growth kinetics, peaking between days two and four, followed by what appears to be a protracted stationary phase.

Figure 3:
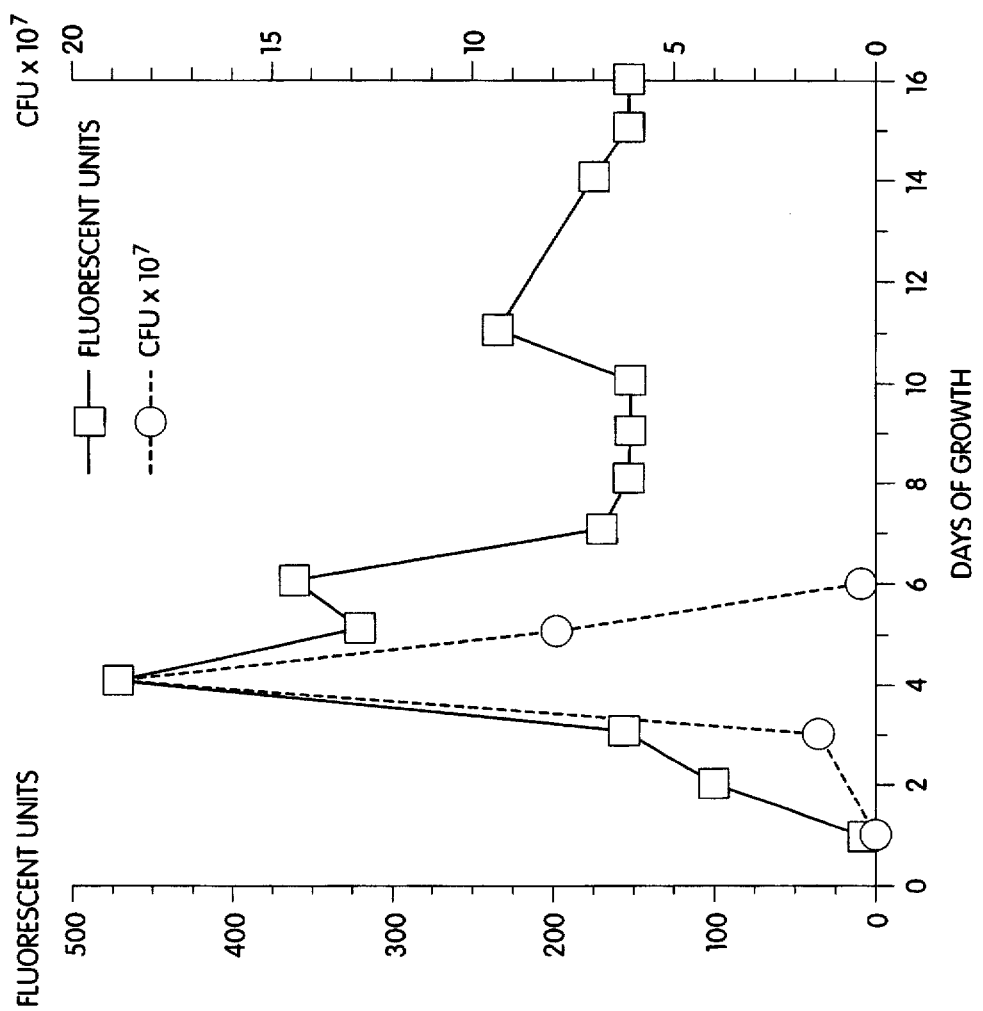
FIG. 3 depicts the correlation between the data received from the fluorometric system and colony formation on agar of *M. hyorhinis*. The correlation coefficient (r), derived from the data of days 1–5, is 0.9467, indicating a high degree of correlation between the flourometer readings and the number of viable organisms prior to the onset of tailing. The symbols are as follows: fluorescent units (□); CFU (o).

In order to determine whether the fluorometric readings would correlate with viability, we plated duplicate samples on agar as described above. FIG. 3 illustrates these data and shows that there is a high degree of correlation between fluorometer readings taken during the log phase of growth and the number of viable organisms present. The data indicate that in this experiment there is a rapid decline in viability of the culture following peak growth and further that viability does not extend beyond the fifth day. These data further suggest that what appears to be a stationary phase is, in fact, an artifact.

In sum, the data indicate that the fluorometric system described, does for broth-grown mycoplasmas what turbidmetric analysis does for larger browth-grown bacteria: it conveniently monitors growth; it correlates with agar growth; but it has the added advantage that the fluorometer readings can be converted to DNA content as well. An additional advantage of this fluorometric system is the fact that once the alkaline EtBr solution is added to the cultural aliquot, the sample can be stored at 4° C. provided it is protected from light. This will allow the accumulation of samples for fluorometry at a later time. When the resuspended cells are in the alkaline/EtBr solution, the strong alkalinity causes the dissolution of the proteins of intact cells releasing the nucleic acids. The alkalinity not only denatures any RNA present but also degrades it, thereby preventing hairpin looping and, thus, any contribution of RNA to EtBr binding. When bound to duplex DNA, the EtBr exhibits a twenty to twenty-five fold increase in its fluorescence than when it is free in solution or in the presence of single-stranded DNA. The procedure is also a rapid one, the time involved in each individual reading, from removal of the sample from the culture to the reading in the fluorometer, being approximately twenty minutes.

Just as with the turbidimetric analysis, the fluorometric data are correlated with viability up to the late log phase of growth. It is also analogous in that we have found the sensitivity of the fluorometric system to closely approximate that of the turbidimetric system used for larger bacteria. That is, when turbidity is first detectable in a bacterial culture, such as $Escherichia$ $coli$, the culture has reached a cell population of approximately $1 \times 10^7$ organisms per ml (Umbreit W. W., (1962), Modern Microbiology, p. 55, W. H. Freeman and Company, San Francisco, Calif.)). However, at that point, initial spectrophotometric readings are nonlinear. Similarly, in our fluorometric method, between $10^7$ and $10^8$ mycoplasmal cells are required before readings can be initiated. One difference between the turbidimetric analysis and this fluorometric method is the fact that while the turbidimetric analysis can easily be saturated requiring dilutions of the culture to be made in order to achieve accurate readings, the fluorometric method is not saturated unless 50 μg/ml or more of DNA is present. It would take upwards of $10^{11}$ cells/ml (approximately 78 μg/ml DNA) before the system would be saturated and require a dilution of the culture.

A major difference between the mycoplasmal growth curve and that of larger bacteria, elucidated by this method, lies in the post peak portion of the curve. Whereas all larger bacteria usually display a decline portion of the growth curve, which has been attributed to exhaustion of vital factors and/or the buildup of toxic products, it is usually preceded by a stationary phase of varying length. Here however, a true stationary phase with mycoplasmas was not apparent, only a decline in viability following peak growth. The tailing seen in FIGS. 2 and 3 was originally thought to be a form of stationary phase of the growth curve. However, after the colony forming units were determined, it was obvious that what was present at this point were nonviable, but intact, mycoplasmal cells or precipitated medium components which were binding DNA. Either alternative is consistent with the methodology because the initial step in the fluorometric method involves centrifugation which would sediment both intact cells and precipitated medium components. However, the former alternative is the more likely since, under the latter, DNA would have to remain intact in a rather hostile environment, given that the mycoplasmal cells would have had to lyse to release the DNA. In addition to $M.$ $hyorhinis$ and $M.$ $fermentans$, we have received essentially the same data for $M.$ $hominus$, $M.$ $orale$, and $Acholeplasma$ $laidlawii$. In each experiment, the mycoplasma reach a peak within three to five days (depending upon the size of the inoculum used) and lost viability following peak growth.

EXAMPLE 2

Determination of nicked vs. Intact Mycoplasmal DNA

It has previously been shown that following inoculation of SP-4 broth with mycoplasmas there is a very rapid period of growth, within 24–48 hours, followed by an equally rapid decline in viability. To determine whether this might be due, in part, from the accumulation of DNA damage, fluorometric assays were conducted. Using the fluorometric assay described above with purified DNA the degree of nicking by comparing fluorometric readings taken before and after boiling the DNA samples in an alkaline ethidium bromide solution could be estimated. Following an initial reading in the fluorometer, a tube containing the alkaline EtBr/cells was boiled for five minutes after which it was quickly cooled in an ice bath. The fluorescence was then reread and the difference was recorded. To be certain nicked DNA was being examined, the mycoplasmal cells were irradiated prior to fluorometric analysis. 4.0 ml of a 24 hour culture of *M. fermentans* was placed in a petri dish which was exposed to X-rays generated using a Phillips X-ray generator with a beryllium window Machlett tube operated at 20 mA yielding a dose rate of 80 Krad/minute. Cells were irradiated for varying times from 20–160 seconds after which aliquots were removed and treated as above for fluorometric analysis, pre- and postboiling, and agar growth.

Table 1 indicates that the sequential irradiation led to a greater than seven log loss in viability over 2.5 minutes of irradiation, indicating that significant DNA damage had been induced.

TABLE 1

Kinetics of Irradiation Killing of
*Mycoplasma fermentans*

| IRRADIATION TIME (SECS.) | COLONY-FORMING- UNITS/ML ± S.D.* |
|---|---|
| 0 | $3.8 \pm 0.37 \times 10^{10}$ |
| 20 | $2.5 \pm 0.8 \times 10^{7}$ |
| 40 | $3.6 \pm 0.06 \times 10^{6}$ |
| 80 | $2.4 \pm 0.16 \times 10^{5}$ |
| 160 | $4.0 \pm 2.0 \times 10^{3}$ |

All samples were taken and treated in triplicate.
*S.D. = Standard deviation

The data in Table 2 show that there was no significant change in the pre- and postboiling fluorometer readings as radiation time increased. That is, there was a 34% change with no irradiation (nicking) and an average of 38.5% thereafter. If nicking of the DNA were responsible, there would have been an increase in the difference between pre- and postboiling samples as irradiation time increased. Thus, although there is a difference between pre- and postboiling samples during culture growth (as seen in Table 1 with no irradiation) this difference, as well as the loss of viability, is not due to accumulated DNA damage.

TABLE 2

Effect of boiling on fluorometer reading
following irradiation of *M. fermentans*
culture

| IRRADIATION TIME (secs.) | FLUOROMETER READING ± S.D.* | | % CHANGE |
|---|---|---|---|
| | PREBOIL | POSTBOIL | |
| 0 | 73 | 48 | 34 |
| 20 | 73 ± 4 | 44 ± 4 | 40 |
| 40 | 64 ± 0.6 | 39 ± 2 | 39 |
| 80 | 69 ± 1 | 42 ± 3 | 39 |
| 160 | 70 ± 0.6 | 45 ± 2 | 36 |

All samples were taken and treated in triplicate.
*S.D. = Standard deviation

With relation to the post-peak portion of the growth curve, it was found that if a sample from this portion of the curve is boiled following the initial reading and then reread, the initial reading will be reduced substantially. Thus, the tailing which is observed in the latter part of the growth curve (and which contains no viable cells) is essentially eliminated. On the contrary, boiling of samples taken from earlier (i.e., pre-peak) portions of the growth curve, where fluorometer readings and viability correlate highly, produces only a small change in the fluorometer reading, indicating that this procedure may, in some systems, prove useful in the assessment of viability. The data in Tables 1 and 2, however, indicate that this correlation should be made with caution as the same number of dead, but intact, cells can produce the same fluorometer reading postboiling. Therefore, each system needs to be evaluated individually should the boiling step be included in a fluorometric regimen.

EXAMPLE 3

Determination of the Effectiveness of an
Antimycoplasmal Antibiotic

The fluorometric system was used to examine the antimycoplasmal activity of chloramphenicol succinate, a water soluble analogue of chloramphenicol. The agent was serially two-fold diluted from 100 µg/ml final concentration in the culture. The growth of a strain of *M. hyorhinis* previously shown to be sensitive to chloramphenicol succinate was then monitored daily as described.

Figure 4:
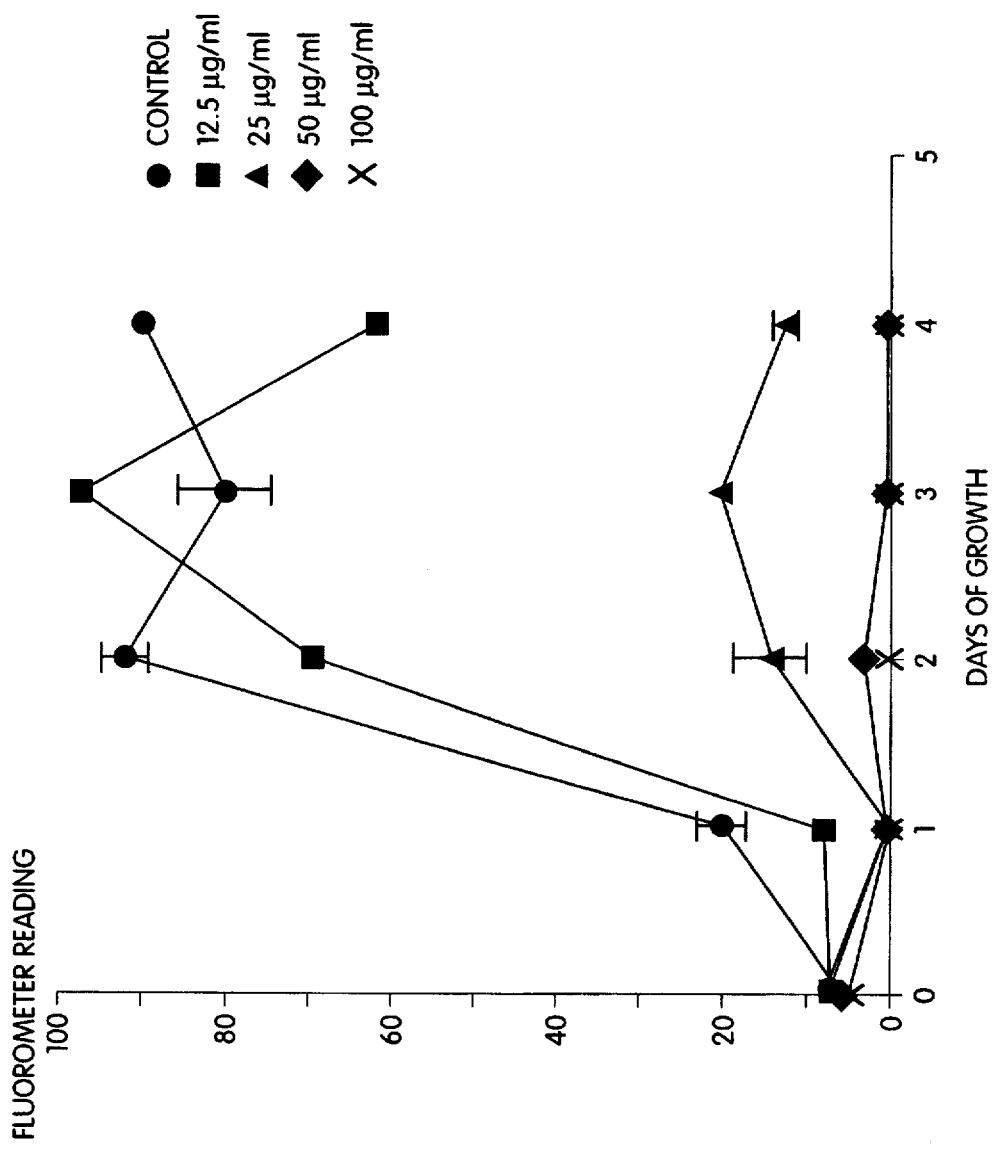
FIG. 4 depicts the effectiveness of chloramphenicol succinate in inhibiting the growth of *M. hyorhinis* using the fluorometric system. The symbols are as follows: control (●); 12.5 μg/ml chloramphenicol succinate (■); 25 μg/ml chloramphenicol succinate (▲); 50 μg/ml chloramphenicol succinate (♦); and 100 μg/ml chloramphenicol succinate (x).

FIG. 4 demonstrates the usefulness of this method for evaluating the efficacy of the antibiotic against mycoplasma. A two-sample T-test, comparing a control to a 12.5 µg/ml curve, the 12.5 µg/ml to the 25 µg/ml curve, the 25 µg/ml to the 50 µg/ml curve and the 50 µg/ml to the 100 µg/ml curve yielded the following results: no significant difference exists between the control and the 12.5 µg/ml curves (p=0.7503); a marginally significant difference exists between the 12.5 µg/ml and 25 µg/ml curves (p=0.0716); a significant difference exists between the 25 µg/ml and 50 µg/ml curves (p=0.0468); and no significant difference exists between the 50 µg/ml and 100 µg/ml curves (p=0.5068). The data show that chloramphenicol succinate is effective. A dose response curve was obtained and doses which are effective, intermediate and ineffective are easily discerned. Agar growth data confirmed the lethality.

EXAMPLE 4

Titration of Yeast Extract

The fluorometric system was used to optimize the SP-4 yeast extract concentration for *M. fermentans*. The recipe for SP-4 calls for 2.5% yeast extract. The concentration was reduced by 75%, 50% and 25% to 0.63%, 1.3% and 1.9% respectively to determine the effect thereon.

Figure 5:
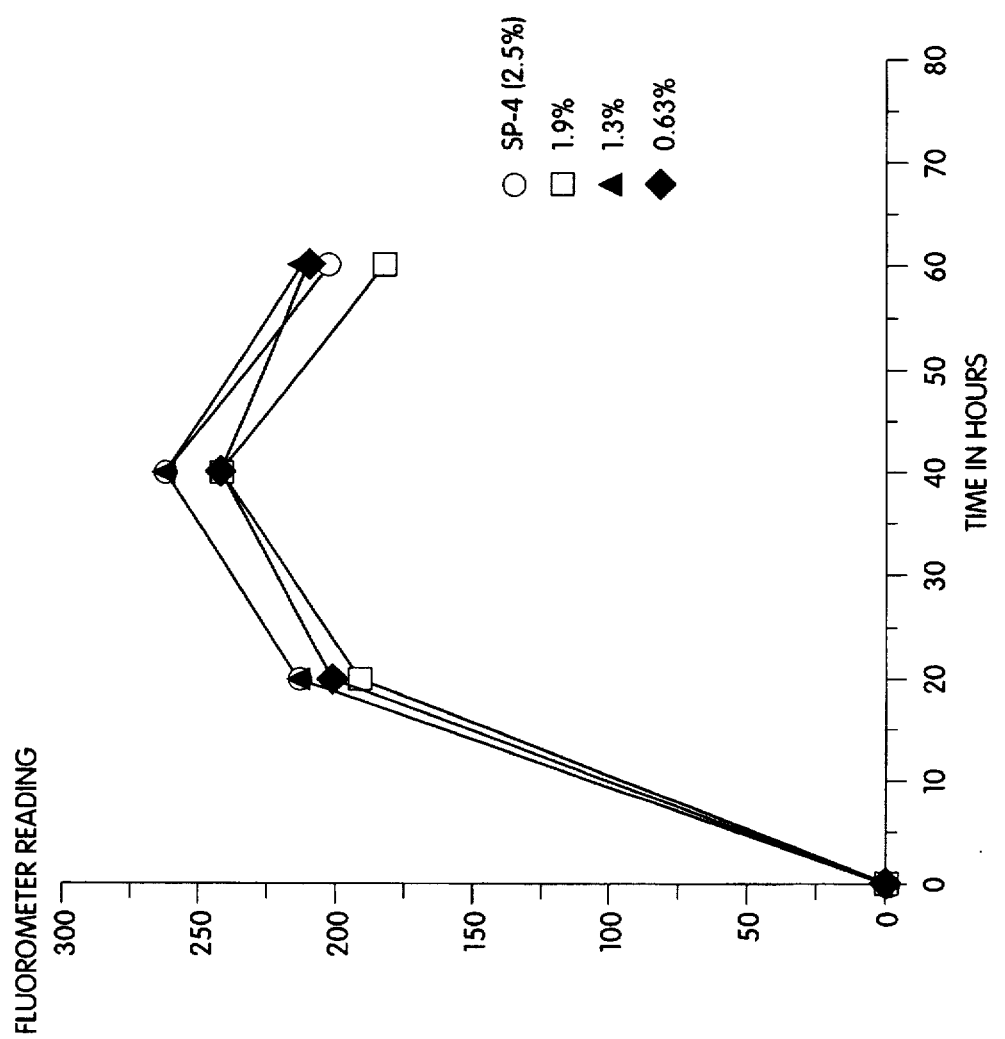
FIG. 5 depicts a two-sample T-test, comparing the growth of *M. fermentans* in the presence of a quantity of yeast extract in the control (SP-4) to three other concentrations of yeast extract. The symbols are as follows: control (SP-4) 2.5% yeast extract concentration (o); 1.9% yeast extract concentration (□); 1.3% yeast extract concentration (▲); and 0.63% yeast extract concentration (♦).

FIG. 5, indicates that there is no significant difference between the yeast extract concentration. The P-values are as follows: comparing 2.5% to 1.9%, yielded p=0.7781; comparing 2.5% to 1.3%, yielded a p=0.9001; comparing 2.5% to 0.63%, yielded a p=0.4885. Thus, it is possible to lower the amount of yeast extract by 75% and still achieve maximal growth of mycoplasma when compared to the complete medium. This system could be used to optimize other medium components in order to develop more defined media than are currently available.

Accordingly, one virtue of this system is that because the fluorometer readings are directly related to DNA content of the sample, it will make possible the standardization of conditions for the growth of mycoplasmas within and between laboratories and for antigenic standardization for eventual vaccines.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of determining the effectiveness of an antimycoplasmal antibiotic, comprising;

culturing pure mycoplasmal cells with an mount of an antimycoplasmal antibiotic;

contacting a sample of the pure culture with a fluorescent DNA intercalating agent under alkaline conditions sufficient to degrade RNA, but not DNA, and maintaining said alkaline conditions, wherein the DNA intercalating agent is in an amount sufficient to be detected when bound to mycoplasmal DNA; and determining the amount of fluorescence emitted by the fluorescent DNA intercalating agent associated with the mycoplasmal DNA as indicative of the number of mycoplasmal cells in the culture.

2. The method of claim 1 wherein the DNA intercalating agent is ethidium bromide.

3. A method of monitoring the growth of mycoplasma in a culture, comprising:

contacting a sample of a pure culture of mycoplasma with a fluorescent DNA intercalating agent under alkaline conditions sufficient to degrade RNA, but not DNA, and maintaining said alkaline conditions, wherein the DNA intercalating agent is in an amount sufficient to be detected when bound to mycoplasmal DNA; and determining the amount of fluorescence emitted by the fluorescent nucleic acid-binding agent associated with the mycoplasmal DNA as indicative of the number of mycoplasmal cells in the culture.

4. The method of claim 3 wherein the DNA intercalating agent is ethidium bromide.

5. The method of claim 4 wherein the sample of the pure culture of mycoplasma is contacted with the ethidium bromide at a pH of from 11 to 12.

6. The method of claim 4 wherein the sample of the pure culture of mycoplasma is contacted with the ethidium bromide at a pH of from 11.8 to 12.

7. The method of monitoring the growth of mycoplasma in a culture, comprising:

contacting a sample of a pure culture of mycoplasma with a solution of 1 µg/ml ethidium bromide at a pH of from 11 to 12 to thereby allow the ethidium bromide to selectively bind to mycoplasmal DNA and to degrade mycoplasmal RNA under alkaline conditions;

maintaining said alkaline conditions; and determining the amount of ethidium bromide associated with the mycoplasmal DNA as indicative of the number of mycoplasmal cells in the culture.

8. A method of monitoring the growth of mycoplasma in a culture, comprising:

preparing a solution of a fluorescent nucleic acid-binding agent, wherein the fluorescent nucleic acid-binding agent is in an amount sufficient to be detected when bound to mycoplasmal DNA;

adjusting the solution to a pH at which mycoplasmal RNA would be degraded, but mycoplasmal DNA would not be degraded;

contacting a sample of a pure culture of mycoplasma with the solution, thereby degrading mycoplasmal RNA but not mycoplasmal DNA, under alkaline conditions;

maintaining said alkaline conditions; and determining the amount of fluorescence emitted by the fluorescent nucleic acid-binding agent associated with the mycoplasmal DNA as indicative of the number of mycoplasmal cells in the culture.

9. The method of claim 8, wherein the pH of the solution is adjusted to from 11 to 12.

10. The method of claim 8, wherein the pH of the solution is adjusted to from 1.18 to 12.

11. The method of claim 8, wherein the nucleic acid binding agent is a DNA intercalating agent.

12. The method of claim 11, wherein the DNA intercalating agent is a phenanthridinium dye.

13. The method of claim 12, wherein the phenanthridinium dye is ethidium bromide.

* * * * *